US010753302B2

(12) United States Patent
Lee et al.

(10) Patent No.: US 10,753,302 B2
(45) Date of Patent: Aug. 25, 2020

(54) METHOD OF ANALYZING FUEL COMPONENT USING AN RF SENSOR FOR A VEHICLE

(71) Applicants: HYUNDAI MOTOR COMPANY, Seoul (KR); KIA MOTORS CORPORATION, Seoul (KR); Jeju National University Industry-Academic Cooperation Foundation, Jeju-si, Jeju-do (KR)

(72) Inventors: Jin Ha Lee, Seoul (KR); Chong Hyun Lee, Jeju-si (KR)

(73) Assignees: HYUNDAI MOTOR COMPANY, Seoul (KR); KIA MOTORS CORPORATION, Seoul (KR); JEJU NATIONAL UNIVERSITY INDUSTRY-ACADEMIC COOPERATION FOUNDATION, Jeju-si, Jeju-Do (KR)

( * ) Notice: Subject to any disclaimer, the term of this patent is extended or adjusted under 35 U.S.C. 154(b) by 7 days.

(21) Appl. No.: 16/202,464

(22) Filed: Nov. 28, 2018

(65) Prior Publication Data
US 2020/0072147 A1 Mar. 5, 2020

(30) Foreign Application Priority Data
Aug. 28, 2018 (KR) .................. 10-2018-0101212

(51) Int. Cl.
*F02D 41/22* (2006.01)
*F02D 41/40* (2006.01)
*G01N 33/28* (2006.01)
*F02P 5/15* (2006.01)

(52) U.S. Cl.
CPC ............. *F02D 41/22* (2013.01); *F02D 41/40* (2013.01); *F02P 5/15* (2013.01); *G01N 33/287* (2013.01); *F02D 2041/224* (2013.01); *F02D 2200/0611* (2013.01)

(58) Field of Classification Search
CPC .... F02D 41/22; F02D 41/40; F02D 2041/224; F02D 2200/0611; G01N 33/287; F02P 5/15
See application file for complete search history.

(56) References Cited

U.S. PATENT DOCUMENTS

| | | | | |
|---|---|---|---|---|
| 3,934,566 A | * | 1/1976 | Ward | F02P 9/007 123/275 |
| 6,320,393 B1 | * | 11/2001 | Yasui | F02D 41/0025 324/663 |
| 2013/0275026 A1 | * | 10/2013 | Methil-Sudhakaran | F02M 65/003 701/103 |

* cited by examiner

*Primary Examiner* — Joseph J Dallo
(74) *Attorney, Agent, or Firm* — Brinks Gilson & Lione

(57) ABSTRACT

A method of analyzing fuel component using an RF (Radio Frequency) sensor for a vehicle includes: receiving a new fuel into a fuel tank so as to mix existing fuel in the fuel tank with the new fuel, measuring a resonance frequency of the mixed fuel using an RF sensor, comparing the measured resonance frequency of the mixed fuel with a resonance frequency of a standard fuel, determining whether the mixed fuel is a normal fuel through the comparison, maintaining an engine combustion pattern corresponding to the standard fuel when the mixed fuel is a normal fuel, and operating reflecting an engine combustion control.

8 Claims, 10 Drawing Sheets

METHOD OF ANALYZING FUEL COMPONENT USING AN RF SENSOR FOR A VEHICLE

CROSS-REFERENCE TO RELATED APPLICATION

This application claims priority to and the benefit of Korean Patent Application No. 10-2018-0101212, filed on Aug. 28, 2018, the entire contents of which are incorporated herein by reference.

FIELD

The present disclosure relates to a method of analyzing fuel component using an RF (Radio Frequency) sensor for a vehicle.

BACKGROUND

The statements in this section merely provide background information related to the present disclosure and may not constitute prior art.

As an RF signal passes through the material between the two antennas, there is a specific resonance frequency that minimizes the reflection coefficient (dB) according to the inherent dielectric constant of the material. All objects have inherent dielectric constants. Gasoline, diesel, kerosene, heavy oil and other automobile fuels also have inherent dielectric constants. Therefore, when the fuel is placed between the RF sensors, the RF sensor has its own resonance frequency depending on the dielectric constant of the fuel.

Also, when the air and the specific fuel are in the RF sensor, the overall dielectric constant changes depending on the amount of air. Therefore, depending on the amount of air, the RF sensor has its own resonance frequency.

On the other hand, there are various methods for discriminating the kind and harmfulness of the fuel. Conventionally, there is a method in which additives are added to a fuel to investigate the components of the fuel using a chemical reaction, the type of the fuel is determined by using an inverted scattering signal of ultrasonic waves, or a method in which the sensor is directly contacted with the fuel.

When chemical reactions are used, it is very complicated and costly to add a chemical sample to check the condition of the fuel. When an inverse scattering signal is used, since there is an indirect method, a fuel having the same reverse scattering power cannot be distinguished from its original limit.

Therefore, these methods cannot be applied to actual automobiles due to problems in cost, difficulty in analyzing the size of equipment, and time desired to install fuel in the vehicle.

We have discovered that, existing automobiles, especially diesel vehicles, do not reflect the sulfur content of diesel fuel on the market, and the sulfur content of the post-treated catalyst is calculated as the sulfur content of the total amount of fuel used for a certain distance operation by determining the average value or a constant value such as 10 ppm.

As a result, the desulfurization engine control is performed so as to recognize more or less of the sulfur content in the sulfur content than the actual sulfur content and to recover the performance deterioration due to sulfur poisoning of the post-treatment catalyst.

For this reason, we have discovered that the desulfurization control of the post-treatment catalyst causes deterioration of fuel consumption, deterioration of post-treatment catalyst, and deterioration of performance.

The above information disclosed in this Background section is only for enhancement of understanding of the background of the present disclosure and therefore it may contain information that does not form the prior art that is already known to a person of ordinary skill in the art.

SUMMARY

The present disclosure provides a method and apparatus for detecting a specific type of fuel or a substance in a fuel by detecting an inherent resonance frequency responsive to a specific dielectric constant of the fuel using an RF sensor. The present disclosure provides a method of analyzing a fuel component using an RF sensor for an vehicle used for improvement of desulfurization combustion control of an engine and maintenance of catalyst performance.

A method of analyzing fuel component using an RF (Radio Frequency) sensor for a vehicle in an exemplary form of the present disclosure includes: receiving a new fuel into a fuel tank so as to mix an existing fuel of the fuel tank with the new fuel, measuring a resonance frequency of the mixed fuel using an RF sensor, comparing the measured resonance frequency of the mixed fuel with a resonance frequency of a standard fuel, determining whether the mixed fuel is a normal fuel through the comparison, maintaining an engine combustion pattern corresponding to the standard fuel if it is determined that the mixed fuel is normal fuel, and operating reflecting an engine combustion control.

Meanwhile, the method may further include after determining whether the mixed fuel is a normal fuel through the comparison, measuring a sulfur content included in the mixed fuel if it is determined that the mixed fuel is not normal fuel, and comparing the measured sulfur content of the mixed fuel with sulfur content information of the standard fuel to derive a difference, and adjusting a desulfurization timing of a catalyst when the mixed fuel is injected.

The RF sensor may be a patch type sensor which includes a first patch sensor attached to one side of the fuel tank and a second patch sensor attached to the outside of the fuel tank to face the first patch sensor.

The RF sensor may be a monopole type sensor which includes a plate patch attached to one side of the fuel tank, and a probe connected to the plate patch and penetrating the inside of the fuel tank to be infiltrated with the fuel.

Meanwhile, a method of analyzing fuel component using an RF sensor for a vehicle according to another exemplary form of the present disclosure includes: receiving a new fuel into a fuel tank so as to mix an existing fuel of the fuel tank with the new fuel, measuring a resonance frequency of the mixed fuel using an RF sensor, comparing the measured resonance frequency of the mixed fuel with a resonance frequency of a standard fuel, determining whether the mixed fuel is a normal fuel through the comparison, determining whether a temperature of the outside air is above a predetermined temperature (e.g., 0° C.) if it is determined that the mixed fuel is the normal fuel, maintaining an engine combustion pattern corresponding to a standard temperature and the standard fuel if it is determined that the temperature of the outside air is above the predetermined temperature (e.g., 0° C.), and operating reflecting an engine combustion control.

Meanwhile, the method of analyzing fuel component using an RF sensor may further include: after determining whether the temperature of the outside air is above the predetermined temperature (e.g., 0° C.), determining a stability of the engine combustion if it is determined that the temperature of the outside air is not above the predetermined temperature (e.g., 0° C.), and notifying that the fuel is defective and alerting that the engine combustion is an abnormal combustion.

In another form, the method may further include: after determining whether the mixed fuel is a normal fuel through the comparison, determining whether the temperature of the outside air is below the predetermined temperature (e.g., 0° C.) if it is determined that the mixed fuel is not the normal fuel, and determining a stability of the engine combustion if it is determined that the temperature of the outside air is not below the predetermined temperature (e.g., 0° C.), notifying that the fuel is defective and warning oiling when the fuel is abnormal, and operating reflecting the engine combustion control if it is determined that the engine combustion is not an abnormal combustion.

In another form, the method may further include after determining whether the temperature of the outside air is below the predetermined temperature (e.g., 0° C.), determining an engine combustion mode corresponding to the combustible fuel with the DI (drivability) value information of the measured fuel when the temperature of the outside air is below the predetermined temperature (e.g., 0° C.), and optimizing combustion and operating reflecting ambient environment and fuel characteristics.

The RF sensor may be a patch type sensor which includes a first patch sensor attached to one side of the fuel tank and a second patch sensor attached to the outside of the fuel tank to face the first patch sensor.

The RF sensor is a monopole type sensor which includes a plate patch attached to one side of the fuel tank, and a probe connected to the plate patch and penetrating the inside of the fuel tank to be infiltrated with the fuel.

According to an exemplary form of the present disclosure, the resonance frequency of the fuel is used to identify the kind of the fuel or the substance in the fuel and precisely distinguish the sulfur content of the diesel so that the post-treatment catalyst of the diesel engine car is poisoned by the sulfur component contained in the diesel, the cycle can be accurately judged, and the desulfurization cycle can be accurately determined.

Thereby, the desulfurization combustion control of the engine can be optimized and the performance of the catalyst can be maintained.

In addition, it is possible to distinguish between general gasoline of gasoline engine vehicle and hi drivability gasoline to optimize engine combustion according to the corresponding fuel.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
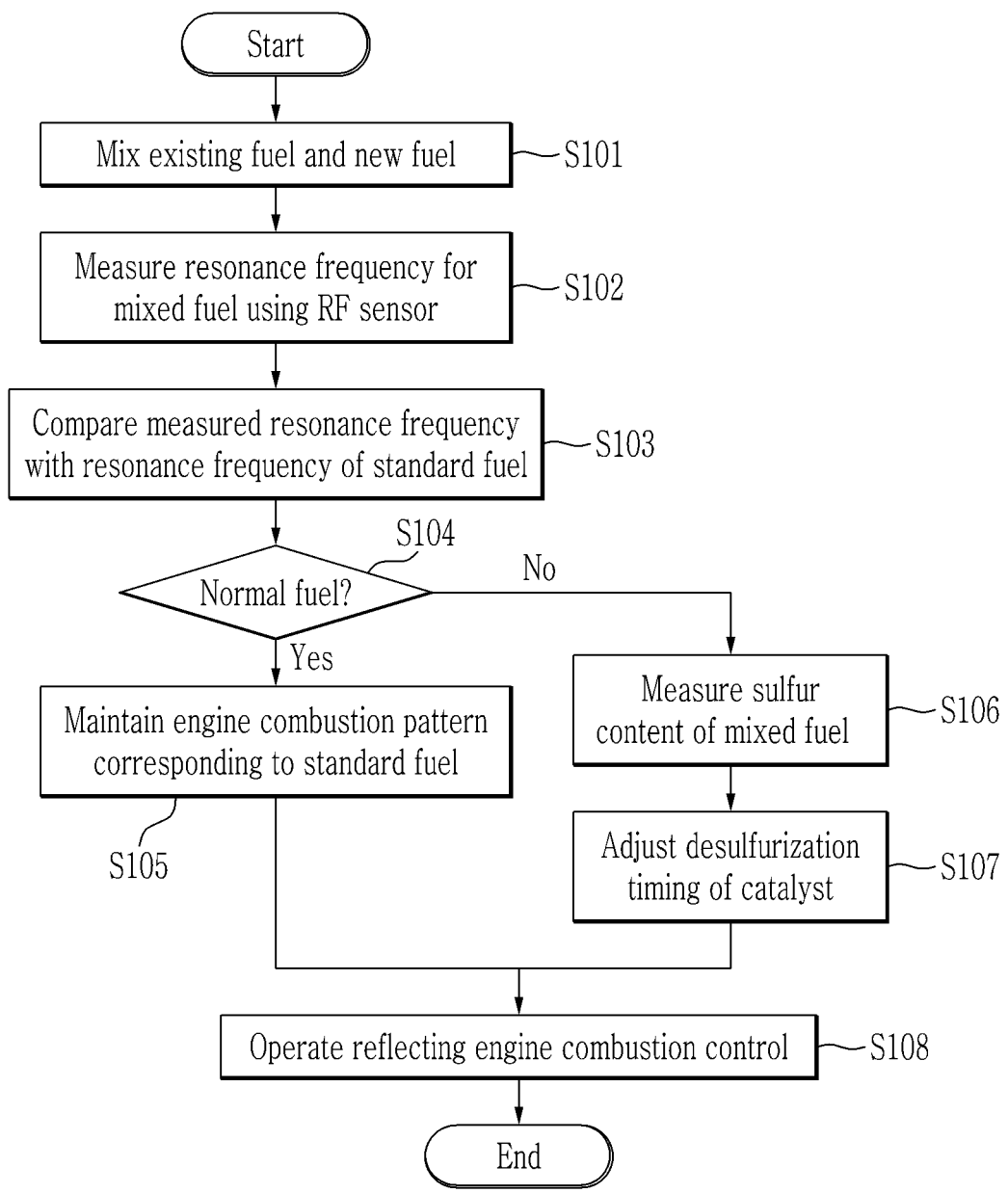
FIG. 1 is a flowchart showing a method of analyzing a fuel component using an RF sensor for a vehicle.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

As those skilled in the art would realize, the described forms may be modified in various different ways, all without departing from the spirit or scope of the present disclosure.

Further, in exemplary forms, since like reference numerals designate like elements having the same configuration, a first exemplary form is representatively described, and in other exemplary forms, only configurations different from the first exemplary form will be described.

The drawings are schematic, and are not illustrated in accordance with a scale. Relative dimensions and ratios of portions in the drawings are illustrated to be exaggerated or reduced in size for clarity and convenience, and the dimensions are just exemplified and are not limiting. In addition, same structures, elements, or components illustrated in two or more drawings use same reference numerals for showing similar features. It will be understood that when an element such as a layer, film, region, or substrate is referred to as being "on" another element, it can be directly on the other element or intervening elements may also be present.

In exemplary forms of the present disclosure, various modifications of the drawings will be expected. Therefore, the exemplary forms are not limited to a specific aspect of the illustrated region, and for example, include modifications of an aspect by manufacturing.

Now, a method of analyzing fuel component using an RF sensor for a vehicle according to an exemplary form of the present disclosure will be described with reference to FIGS. 1 to 4.

Figure 2:
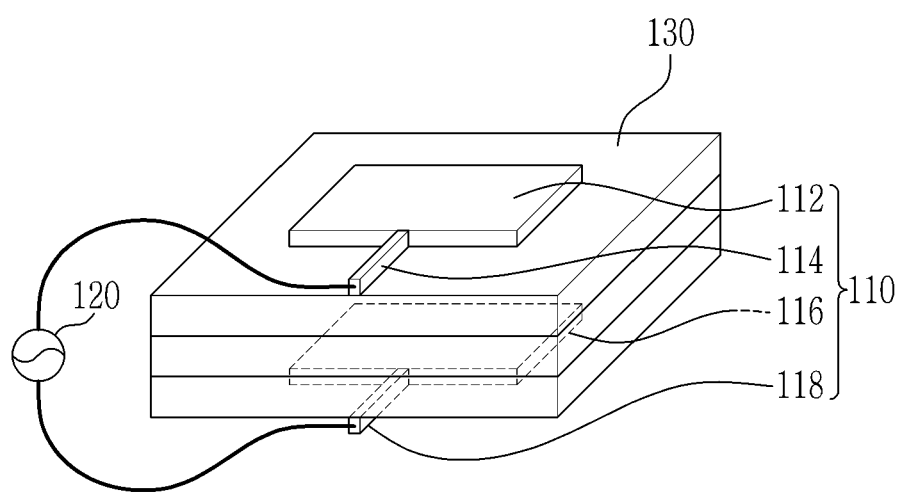
FIG. 2 is a view schematically showing a patch type RF sensor installed in a fuel tank.
Figure 3:
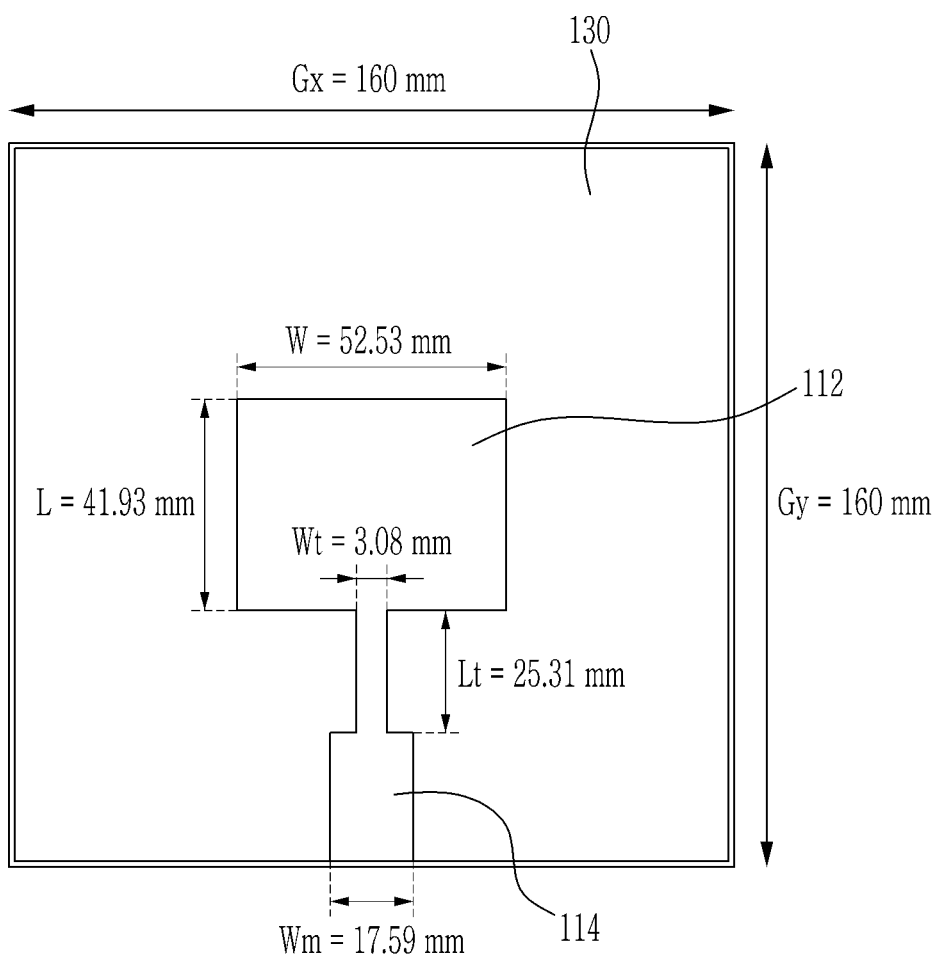
FIG. 3 is a diagram illustrating a design example of a patch type RF sensor.
Figure 4:
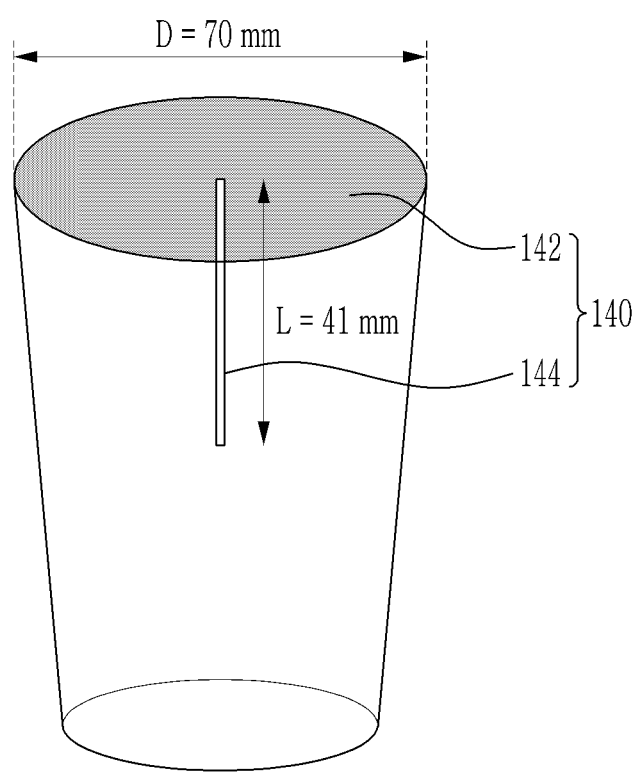
FIG. 4 is a diagram illustrating a design example of a monopole type RF sensor.

FIG. 1 is a flowchart showing a method of analyzing a fuel component using an RF sensor for a vehicle, FIG. 2 is a view schematically showing a patch type RF sensor installed in a fuel tank, FIG. 3 is a diagram illustrating a design example of a patch type RF sensor, and FIG. 4 is a diagram illustrating a design example of a monopole type RF sensor.

Referring to FIG. 1, in a method of analyzing fuel component using an RF sensor for a vehicle according to an exemplary form of the present disclosure, firstly, a new fuel is injected into a fuel tank containing the fuel and the existing fuel is mixed with the new fuel S101.

In one form, the method of analyzing a fuel component may be performed or implemented by a controller including at least one processor operated by a setting program, in which the setting program includes a series of commands for performing each step included in the method according to the present disclosure to be described below.

The existing fuels may be common commercial diesel. The existing fuels have inherent sulfur content, and if the sulfur content of the new fuel differs from the sulfur content of the existing fuel, the sulfur content of the mixed fuel after mixing the existing fuel with the new fuel will be different from the sulfur content of the existing fuel.

Then, a resonance frequency for the mixed fuel is measured using an RF sensor S102. Diesel has inherent dielectric constant, and inherent resonance frequency is measured by the RF sensor according to the dielectric constant. The existing fuel has inherent dielectric constant and inherent resonance frequency, and mixed fuel has different dielectric constant from existing fuel, so resonant frequency different from existing fuel is measured.

Then, the measured resonance frequency is compared with a resonance frequency of a standard fuel S103. The resonance frequency of the standard fuel is measured by repeatedly measuring the resonance frequency of the existing fuel by an experiment using an RF sensor and then converting it into an average resonance frequency value.

Then, it is determined whether the mixed fuel is a normal fuel through the comparison S104. That is, it is determined whether the mixed fuel is the same as the standard fuel. If the new fuel is mixed with the existing fuel but shows the same resonance frequency as the standard fuel, the mixed fuel is determined to be normal. However, if the mixed fuel has a resonant frequency different from that of the standard fuel, the mixed fuel is determined to be an abnormal fuel.

Then, the engine combustion pattern corresponding to the standard fuel is maintained if it is determined that the mixed fuel is normal fuel S105.

Then, operation is performed reflecting an engine combustion control S108. The engine combustion control in the gasoline engine may be performed by adjusting the fuel injection amount and adjusting the ignition timing of the spark plug. For example, in the case of a multi-point injection (MPI) engine of a serial 4-cylinder type, the fuel injection amount increases when the fuel injection period is lengthened. In the case of a gasoline direct injection (GDI) engine that is a direct injection type gasoline engine, the injection amount can be increased by adjusting the period of the fuel injection. Further, the ignition timing of the spark plug can be adjusted while advancing or retarding based on the peak of the engine piston.

Meanwhile, the sulfur content included in the mixed fuel is measured if it is determined that the mixed fuel is not normal fuel S106. It is determined that the sulfur content is 100% poisoned by the nitrogen oxide storage catalyst (LNT), the diesel oxidation catalyst (DOC) and the like when theoretically a fuel of 50 ppm or less is used. In this case, when $SO_2$ or the like is measured at the downstream end of the catalyst, it is confirmed that the total amount is poisoned at 0 ppm. However, since the sulfur is slipped to the downstream end of the catalyst, the $SO_2$ is measured at the downstream end of the catalyst.

Therefore, it is possible to measure the sulfur content contained in the mixed fuel from the $SO_2$ detected by the $SO_2$ detector and the mixed fuel consumption amount during the engine operation by providing the $SO_2$ detector at the downstream of the LNT, DOC, etc.

Then, the sulfur content of the measured mixed fuel is compared with the sulfur content information of the standard fuel to derive the difference, and the desulfurization timing of the catalyst is adjusted when the mixed fuel is injected S107.

In the case of a standard fuel having a specific sulfur content, the desulfurization timing of the catalyst is set in advance according to the sulfur content, and the desulfurization timing of the catalyst can be adjusted according to the sulfur content contained in the mixed fuel.

Meanwhile, the RF sensor 110 according to an exemplary form of the present disclosure may include a first patch sensor 112 and a second patch sensor 116, as shown in FIG. 2. The first patch sensor 112 may be attached to one side of the fuel tank, and the second patch sensor 116 may be attached to the outside of the fuel tank to face the first patch sensor 112. The first patch sensor 112 and the second patch sensor 116 may be connected to the function generator 120 through the ground patches 114 and 118. The function generator 120 can functionally convert the electrical signals of the fuel contained in the fuel tank detected by the first patch sensor 112 and the second patch sensor 116.

As shown in FIG. 3, the RF sensor 110 may be attached to the acrylic plate 130 and the acrylic plate 130 may be attached to the outside of the fuel tank. For example, the acrylic plate 130 may have a width Gx of about 160 mm and a length Gy of about 160 mm, and the lateral width W of the first patch sensor 112 and the second patch sensor 116 may be set to have a vertical width L of about 41.93 mm, and the ground patches 114 and 118 may be set to the shape, length, and width shown in FIG. 3.

Meanwhile, the RF sensor 140 may be a monopole type sensor which includes a plate patch 142 attached to one side of the fuel tank container, a plate patch 142 connected to the plate patch 142, and a probe 144 penetrating into the interior of the vessel and infiltrating the fuel. The diameter D of the plate patch 142 may be set to about 70 mm and the length "L" of the probe 144 may be set to about 41 mm.

The patch type RF sensor 110 and the monopole type RF sensor 140 may be respectively installed at the outside of the fuel tank to measure the resonance frequency of the fuel in the method of analyzing fuel component.

Figure 5:
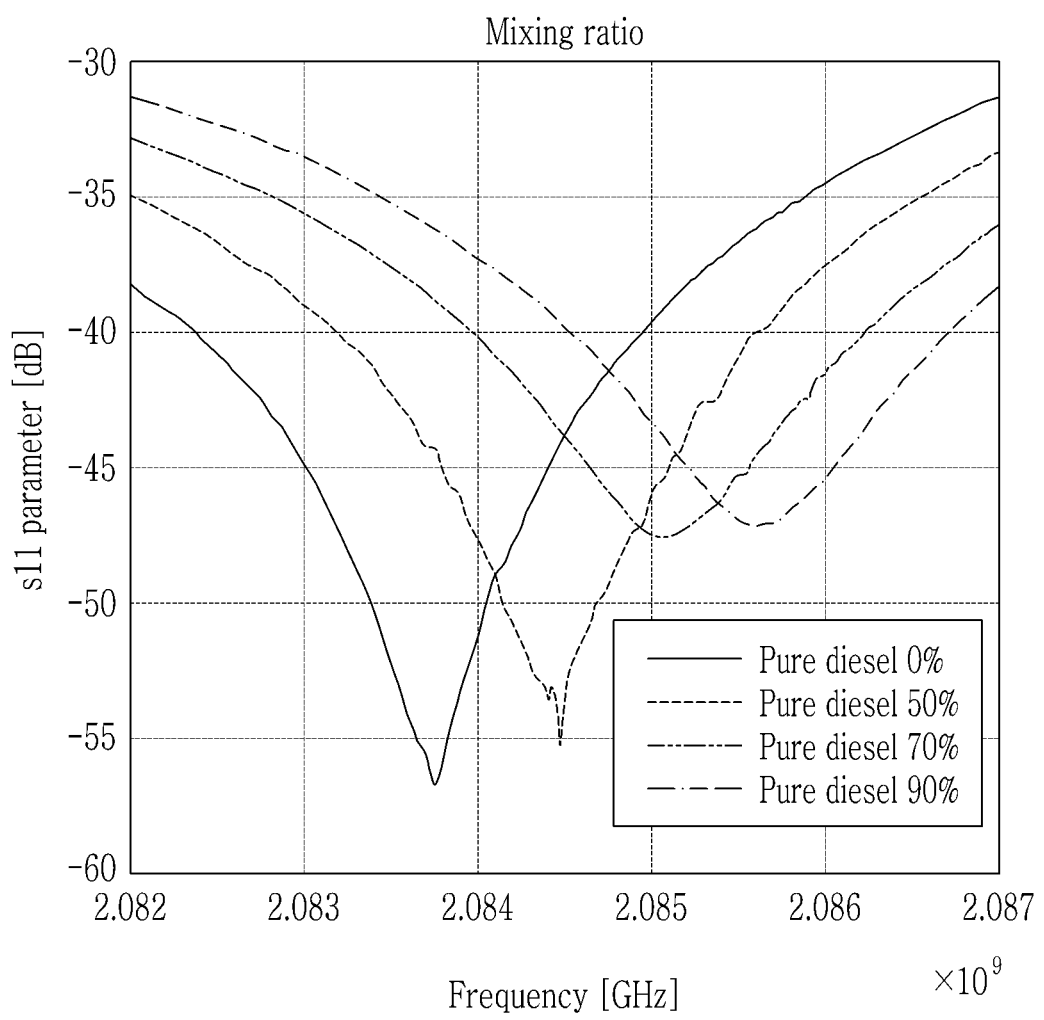
FIG. 5 is a graph showing a change in resonance frequency measured by a patch type RF sensor with respect to the mixing ratios of general commercial diesel and ship oil (inherent sulfur)
Figure 6:
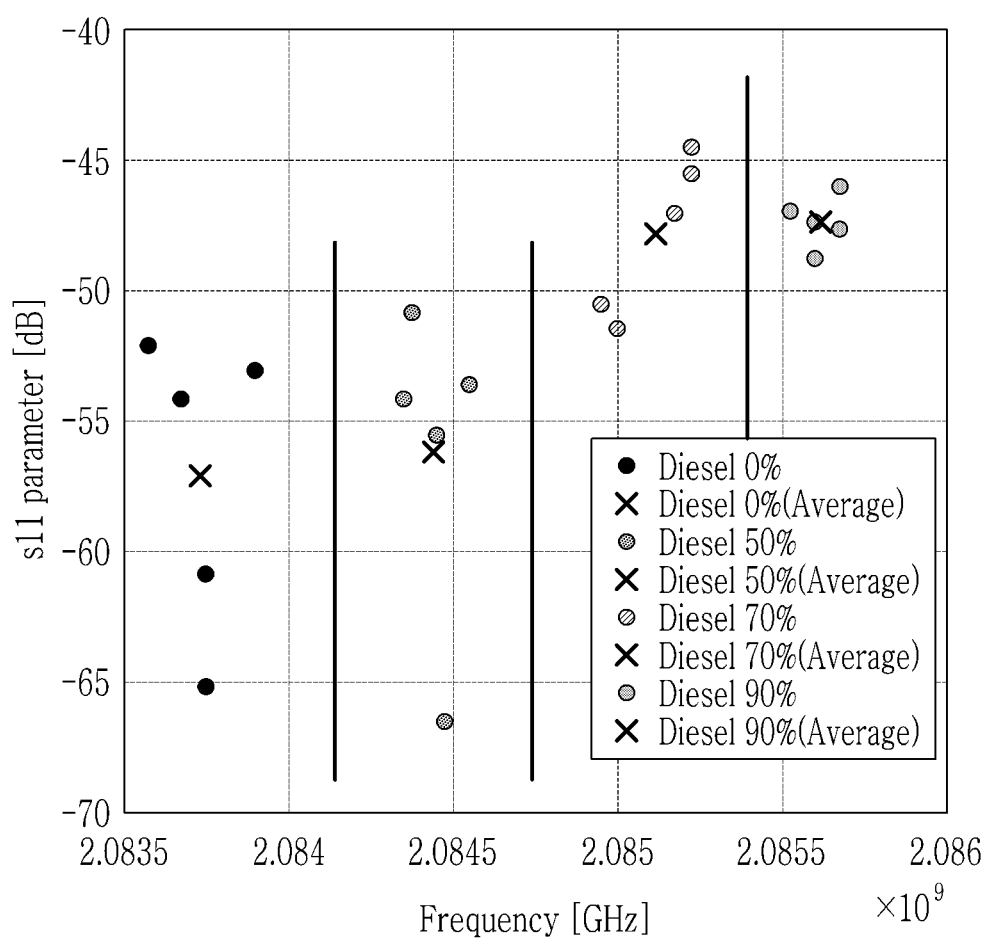
FIG. 6 is a graph showing a resonance frequency and an average resonance frequency measured several times by a patch type RF sensor for each mixing ratio of a common commercial diesel and a marine oil (inherent sulfur)

FIG. 5 is a graph showing a change in resonance frequency measured by a patch type RF sensor according to an exemplary form of the present disclosure, with respect to the mixing ratios of general commercial diesel and ship oil (inherent sulfur), and FIG. 6 is a graph showing a resonance frequency and an average resonance frequency measured several times by a patch type RF sensor according to an exemplary form of the present disclosure, for each mixing ratio of a common commercial diesel and a marine oil (inherent sulfur).

As shown in FIG. 5, when the pure diesel is 0%, the specific resonance frequency at which the reflection coefficient (s11 parameter) becomes minimum is about 2.08375 GHz, where the minimum reflection coefficient is about −56.75 dB. When the pure diesel is 50%, the specific resonance frequency is about 2.08447 GHz, where the minimum reflection coefficient is about −55.29 dB. When the pure diesel is 70%, the specific resonance frequency is about 2.08504 GHz, where the minimum reflection coefficient is about −47.58 dB. Further, when the pure diesel is 90%, the specific resonance frequency is about 2.08560 GHz, where the minimum reflection coefficient is about −47.21 dB. As described above, it can be confirmed that the resonance frequency at which the reflection coefficient becomes minimum varies depending on the sulfur content in the diesel.

As shown in FIG. 6, It is possible to derive the average resonance frequency at the minimum reflection coefficient by measuring the resonance frequency several times according to the mixing ratio of diesel and ship oil (inherent sulfur) by experiment.

Figure 7:
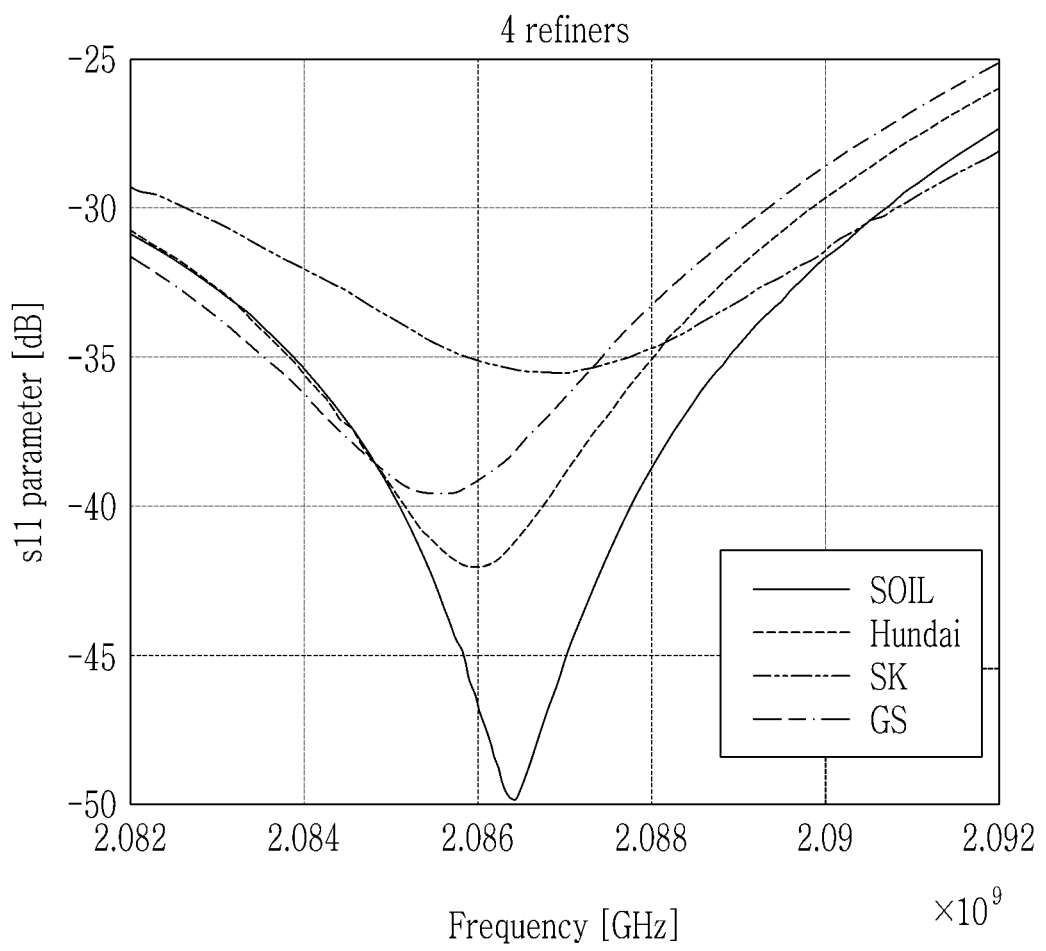
FIG. 7 is a graph showing changes in resonance frequency measured by a patch type RF sensor according to oil refiner of a general commercial diesel.
Figure 8:
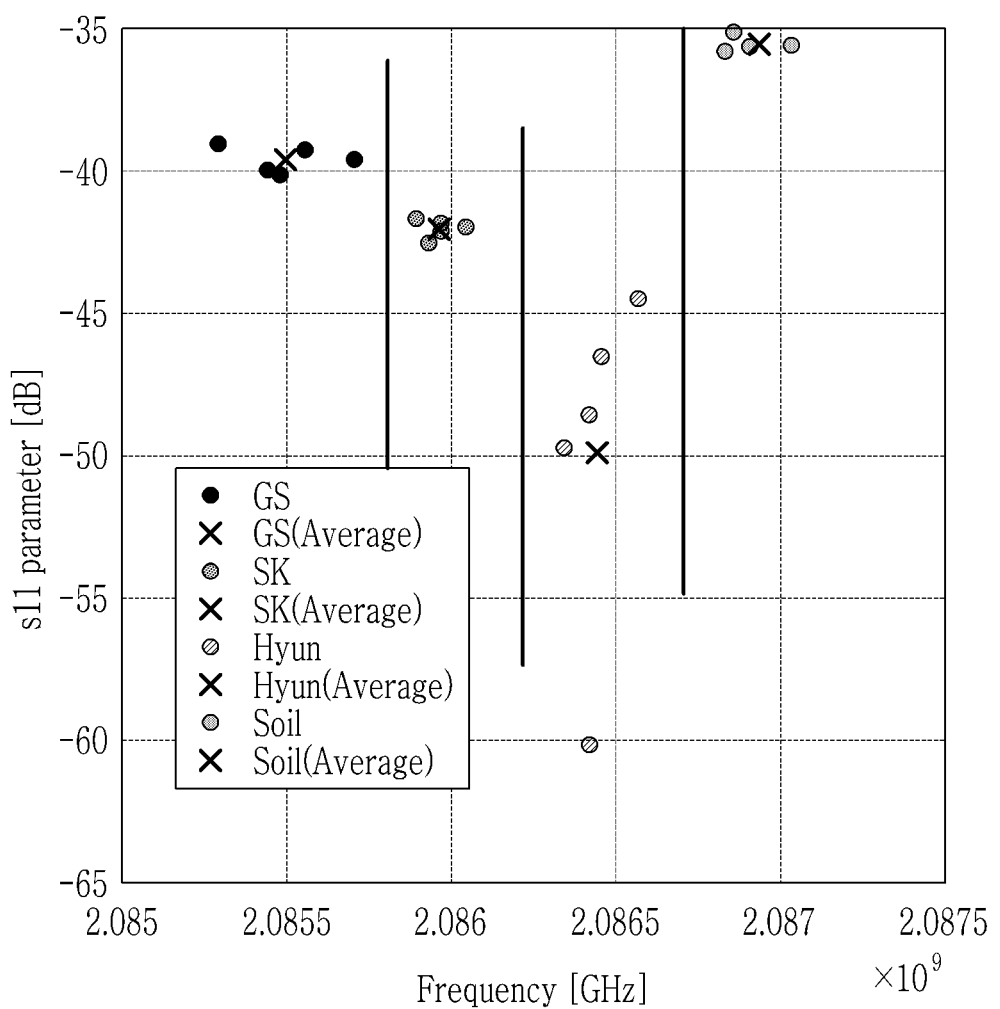
FIG. 8 is a graph showing the resonance frequency and the average resonance frequency measured several times by the patch type RF sensor by refiners of the general commercial diesel.

FIG. 7 is a graph showing changes in resonance frequency measured by a patch type RF sensor according to an exemplary form of the present disclosure, according to oil refiner of a general commercial diesel, and FIG. 8 is a graph showing the resonance frequency and the average resonance frequency measured several times by the patch type RF sensor according to one form of the present disclosure, by refiners of the general commercial diesel.

FIG. 7 and FIG. 8 show changes in the resonance frequency of refineries of general commercial diesel. In the case of GS company, the specific resonance frequency of diesel having the minimum reflection coefficient is about 2.08556 GHz, where the minimum reflection coefficient is about −39.59 dB. In the case of Hyundai company, the resonant frequency of diesel is about 2.08597GHz, and the minimum reflection coefficient is about −42.03dB. In the case of Soil company, the resonant frequency of diesel is about 2.08642GHz, and the minimum reflection coefficient is about −49.85dB. Further, in the case of SK company, the resonant frequency of diesel is about 2.08642GHz, and the minimum reflection coefficient is about −35.52dB. Like this, it can be seen that the resonance frequency of the diesel with the minimum reflection coefficient for each refiner is different, and the sulfur content contained in diesel is different.

As shown in FIG. 8, the resonance frequency of the oil refiner and the diesel can be measured several times by experiments to derive the average resonance frequency of the diesel at the minimum reflection coefficient.

Figure 9:
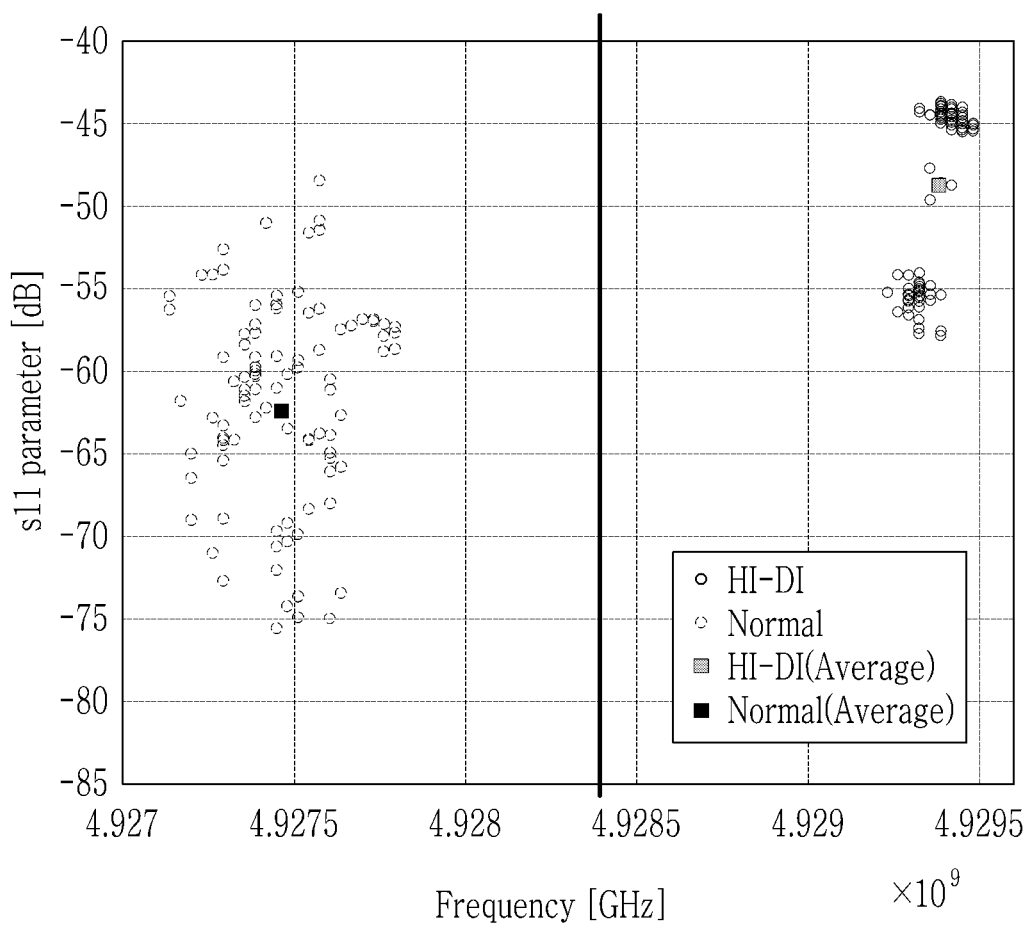
FIG. 9 is a graph showing the resonance frequency and the average resonance frequency measured several times by the patch type RF sensor with respect to the gasoline general fuel and the extreme high mileage gasoline fuel.

FIG. 9 is a graph showing the resonance frequency and the average resonance frequency measured several times by the patch type RF sensor according to an exemplary form of the present disclosure, with respect to the gasoline general fuel and the extreme high mileage gasoline fuel.

As shown in FIG. 9, the average resonance frequency of the gasoline general fuel with the minimum reflection coefficient is about 4.927 GHz and the average resonance frequency of the extreme high mileage gasoline fuel is about 4.929 GHz. and the resonance frequency difference between gasoline general fuel and extreme high mileage gasoline fuel is about 1.915 MHz. As described above, even in the case of gasoline fuel, the resonance frequency is different according to the difference of the dielectric constant, and the combustion can be optimized and operated according to the gasoline fuel type discriminated by the resonance frequency.

Figure 10:
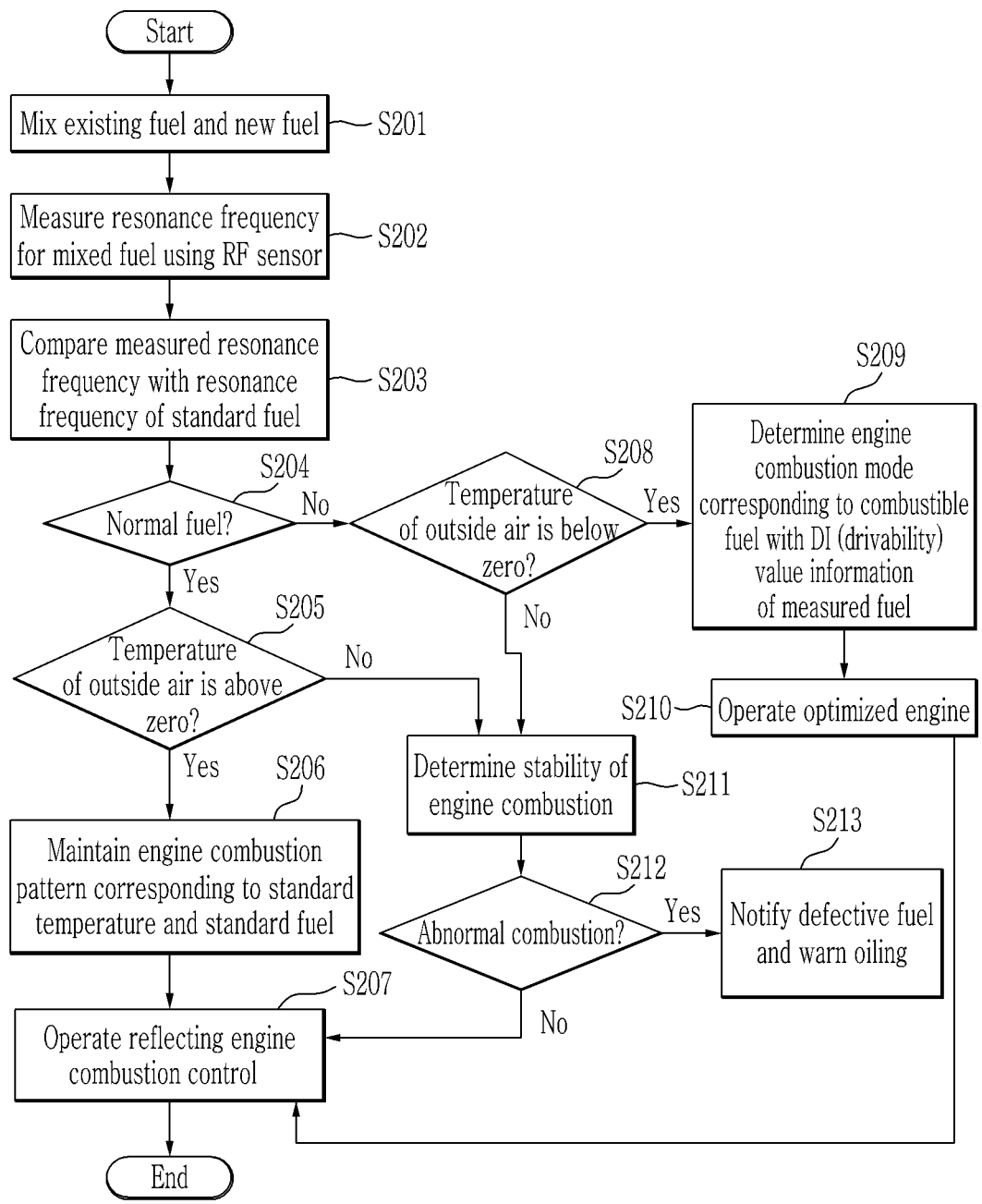
FIG. 10 is a flowchart showing a method of analyzing fuel component using an RF sensor for a vehicle.

FIG. 10 is a flowchart showing method of analyzing fuel component using an RF sensor for a vehicle according to another form of the present disclosure.

Referring to FIG. 10, in a method of analyzing fuel component using an RF sensor for a vehicle in another form of the present disclosure, firstly, a new fuel is injected into a fuel tank containing the fuel and the existing fuel is mixed with the new fuel S201. The existing and new fuels may be gasoline fuels.

Then, a resonance frequency for the mixed fuel is measured using an RF sensor S202. As shown in FIG. 9, general commercial gasoline fuels and extreme high mileage gasoline fuels have different resonant frequencies depending on their inherent dielectric constant. Further, the existing fuel has inherent dielectric constant and inherent resonance frequency, and mixed fuel has different dielectric constant from existing fuel, so resonant frequency different from existing fuel is measured.

Then, the measured resonance frequency is compared with a resonance frequency of a standard fuel S203. The resonance frequency of the standard fuel is measured by repeatedly measuring the resonance frequency of the existing fuel by an experiment using an RF sensor and then converting it into an average resonance frequency value. The resonance frequency of the standard fuel is data obtained by taking into account external environmental information (temperature, humidity) and characteristics of resonance frequency values of various commercial standard fuels and DI values of various fuels.

Then, it is determined whether the mixed fuel is a normal fuel through the comparison S204. That is, it is determined whether the mixed fuel is the same as the standard fuel. If the new fuel is mixed with the existing fuel but shows the same resonance frequency as the standard fuel, the mixed fuel is determined to be normal. However, if the mixed fuel has a resonant frequency different from that of the standard fuel, the mixed fuel is determined to be an abnormal fuel.

Then, it is determined whether the temperature of the outside air is above a predetermined temperature, for example zero (0) ° C., if it is determined that the mixed fuel is normal fuel S205.

Then, the engine combustion pattern corresponding to the standard temperature and the standard fuel is maintained if it is determined that the temperature of the outside air is above the predetermined temperature (e.g., 0° C.) S206.

Then, operation is performed reflecting an engine combustion control S207. The engine combustion control in the gasoline engine may be performed by adjusting the fuel injection amount and adjusting the ignition timing of the spark plug. For example, in the case of an MPI engine of a serial 4-cylinder type, the fuel injection amount increases when the fuel injection period is lengthened. In the case of a GDI engine that is a direct injection type gasoline engine, the injection amount can be increased by adjusting the period of the fuel injection. Further, the ignition timing of the spark plug can be adjusted while advancing or retarding based on the peak of the engine piston.

After determining whether the temperature of the outside air is above zero the predetermined temperature (e.g.,0° C.), the stability of the engine combustion is determined if it is determined that the temperature of the outside air is not above the predetermined temperature (e.g.,0° C.) S211.

Then, it is determined whether the engine combustion is abnormal S212, and it is notified that the fuel is defective and warning oiling if it is determined that the fuel is abnormal S213. However, operating reflecting an engine combustion control is performed if it is determined that the combustion is not an abnormal combustion S207.

After determining whether the mixed fuel is a normal fuel through the comparison S204, it is determined whether the temperature of the outside air is below the predetermined temperature (e.g.,0° C.)if it is determined that the mixed fuel is not normal fuel S208.

Then, the stability of the engine combustion is determined if it is determined that the temperature of the outside air is not below the predetermined temperature (e.g.,0° C.) S211, it is determined whether the engine combustion is abnormal S212, and it is notified that the fuel is defective and warning oiling if it is determined that the fuel is abnormal S213. However, operating reflecting an engine combustion control is performed if it is determined that the combustion is not an abnormal combustion S207.

At this time, the engine combustion mode corresponding to the combustible fuel is determined with the DI (drivability) value information of the measured fuel S209, and combustion and operating is optimized reflecting ambient environment and fuel characteristics S210.

In the method of analyzing fuel component according to another exemplary form of the present disclosure, the patch type RF sensor 110 and the monopole type RF sensor 140 shown in FIGS. 2 and 3 may be respectively or at the same time installed outside the fuel tank to measure the resonance frequency of the fuel.

Like this, in the method of analyzing fuel component according to another exemplary form of the present disclosure, it is possible to judge whether the mixed fuel injected into the fuel tank is normal quality and discriminate whether the fuel is general gasoline fuel or extreme high mileage gasoline fuel and correspondingly combustion optimization operation is possible.

Like this, according to an exemplary form of the present disclosure, the resonance frequency of the fuel is used to identify the kind of the fuel or the substance in the fuel and precisely distinguish the sulfur content of the diesel so that the post-treatment catalyst of the diesel engine car is poisoned by the sulfur component contained in the diesel, the cycle can be accurately judged, and the desulfurization cycle can be accurately determined.

Thereby, the desulfurization combustion control of the engine can be optimized and the performance of the catalyst can be maintained.

In addition, it is possible to distinguish between general gasoline of gasoline engine vehicle and hi drivability gasoline to optimize engine combustion according to the corresponding fuel.

While this present disclosure has been described in connection with what is presently considered to be practical exemplary forms, it is to be understood that the present disclosure is not limited to the disclosed forms. On the contrary, it is intended to cover various modifications and equivalent arrangements included within the spirit and scope of the present disclosure.

DESCRIPTION OF SYMBOLS

| | |
|---|---|
| 110: patch type RF sensor | 112: first patch sensor |
| 114, 118: ground patch | 116: second patch sensor |
| 120: function generator | 130: acryl plate |
| 140: monopole type RF sensor | 142: plate patch |
| 144: probe | |

What is claimed is:

1. A method of analyzing a fuel component using an RF (Radio Frequency) sensor for a vehicle, the method comprising:
   receiving a new fuel into a fuel tank so as to mix an existing fuel of the fuel tank with the new fuel;
   measuring a resonance frequency of the mixed fuel using an RF sensor;
   comparing the measured resonance frequency of the mixed fuel with a resonance frequency of a standard fuel;
   determining whether the mixed fuel is a normal fuel;
   maintaining an engine combustion pattern corresponding to the standard fuel when the mixed fuel is determined as the normal fuel;
   operating reflecting an engine combustion control;
   after determining whether the mixed fuel is a normal fuel, measuring a sulfur content included in the mixed fuel when the mixed fuel is not the normal fuel;
   comparing the measured sulfur content of the mixed fuel with sulfur content information of the standard fuel to derive a difference; and
   adjusting a desulfurization timing of a catalyst when the mixed fuel is injected.

2. The method of claim 1, wherein:
   the RF sensor is a patch type sensor which includes a first patch sensor attached to one side of the fuel tank and a second patch sensor attached to an outside of the fuel tank to face the first patch sensor.

3. The method of claim 1, wherein:
   the RF sensor is a monopole type sensor which includes a plate patch attached to one side of the fuel tank, and a probe connected to the plate patch and penetrating an inside of the fuel tank to be infiltrated with the fuel.

4. A method of analyzing a fuel component using an RF (Radio Frequency) sensor for a vehicle, the method comprising:
   receiving a new fuel into a fuel tank so as to mix an existing fuel of the fuel tank with the new fuel;
   measuring a resonance frequency of the mixed fuel using an RF sensor;
   comparing the measured resonance frequency of the mixed fuel with a resonance frequency of a standard fuel;
   determining whether the mixed fuel is a normal fuel;
   determining whether a temperature of an outside air is above a predetermined temperature when the mixed fuel is determined as the normal fuel,
   maintaining an engine combustion pattern corresponding to a standard temperature and the standard fuel when the temperature of the outside air is above the predetermined temperature;
   operating reflecting an engine combustion control;
   after determining whether the temperature of the outside air is above the predetermined temperature, determining a stability of the engine combustion when the temperature of the outside air is not above the predetermined temperature; and
   notifying that the fuel is defective and alerting that the engine combustion is an abnormal combustion.

5. The method of claim 4, further comprising:
   after determining whether the mixed fuel is the normal fuel, determining whether the temperature of the outside air is below the predetermined temperature when the mixed fuel is not the normal fuel;
   determining the stability of the engine combustion when the temperature of the outside air is not below the predetermined temperature;
   notifying that the fuel is defective and warning oiling when the fuel is abnormal; and
   operating reflecting the engine combustion control when the engine combustion is not an abnormal combustion.

6. The method of claim 5, further comprising:
   after determining whether the temperature of the outside air is below the predetermined temperature, determining an engine combustion mode corresponding to a combustible fuel with DI (drivability) value information of the measured fuel when the temperature of the outside air is below the predetermined temperature; and optimizing combustion and operating reflecting ambient environment and fuel characteristics.

7. The method of claim 4, wherein the RF sensor is a patch type sensor which includes a first patch sensor attached to one side of the fuel tank and a second patch sensor attached to an outside of the fuel tank to face the first patch sensor.

8. The method of claim 4, wherein the RF sensor is a monopole type sensor which includes a plate patch attached to one side of the fuel tank, and a probe connected to the plate patch and penetrating an inside of the fuel tank to be infiltrated with the fuel.

* * * * *